(12) United States Patent
SaNogueira et al.

(10) Patent No.: US 6,447,760 B2
(45) Date of Patent: Sep. 10, 2002

(54) SUNLESS TANNING COMPOSITIONS

(75) Inventors: James SaNogueira, Suffern, NY (US); Thomas Russo, Wharton, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/845,645

(22) Filed: Apr. 30, 2001

Related U.S. Application Data

(60) Provisional application No. 60/202,403, filed on May 8, 2000.

(51) Int. Cl.$^7$ .............................. A61K 7/42; A61K 7/44; A61K 7/00
(52) U.S. Cl. ........................... 424/59; 424/60; 424/400; 424/401
(58) Field of Search ........................ 424/59, 60, 400, 424/401

(56) References Cited

U.S. PATENT DOCUMENTS

| | | | |
|---|---|---|---|
| 4,481,185 A | 11/1984 | Grollier et al. | 424/59 |
| 4,515,773 A | 5/1985 | Herlihy | 424/59 |
| 4,609,544 A | 9/1986 | Herlihy | 424/59 |
| 4,708,865 A | 11/1987 | Turner | 424/59 |
| 4,880,621 A | 11/1989 | Grollier et al. | 424/74 |
| 4,933,177 A | 6/1990 | Grollier et al. | 424/74 |
| 5,015,263 A | 5/1991 | Albrecht et al. | 8/680 |
| 5,215,759 A | 6/1993 | Mausner | 424/489 |
| 5,232,688 A | 8/1993 | Ziegler et al. | 424/59 |
| 5,302,378 A | 4/1994 | Crotty et al. | 424/59 |
| 5,458,872 A | 10/1995 | Durand | 424/59 |
| 5,514,367 A | 5/1996 | Lentini et al. | 424/59 |
| 5,514,437 A | 5/1996 | Tanner et al. | 424/63 |
| 5,569,460 A | 10/1996 | Kurz et al. | 424/401 |
| 5,603,923 A | 2/1997 | Robinson et al. | 424/60 |
| 5,612,044 A | 3/1997 | Suares et al. | 424/401 |
| 5,620,681 A | 4/1997 | Takata et al. | 424/59 |
| 5,645,822 A | 7/1997 | Meyer et al. | 424/59 |
| 5,662,890 A | 9/1997 | Punto et al. | 424/59 |
| 5,700,452 A | 12/1997 | Deckner et al. | 424/59 |
| 5,741,480 A | 4/1998 | Ascione | 424/59 |
| 5,750,092 A | 5/1998 | Meyer et al. | 424/59 |
| 5,827,506 A | 10/1998 | McShane et al. | 424/59 |
| 5,834,013 A | 11/1998 | Ribier et al. | 424/450 |
| 5,958,383 A | 9/1999 | McEleney et al. | 424/59 |
| 6,033,650 A | 3/2000 | Calello et al. | 424/64 |
| 6,190,678 B1 * | 2/2001 | Hasenoehrl et al. | 424/401 |
| 6,214,322 B1 * | 4/2001 | Castro et al. | 424/59 |
| 6,264,934 B1 * | 7/2001 | Kantner et al. | 424/78.03 |

FOREIGN PATENT DOCUMENTS

WO   WO98/23256   6/1998

OTHER PUBLICATIONS

Database KOSMET on STN, AN 11430. Kurtz, T. "Formulating Effective Self–Tanners with DHA". Abstract, Cosmet Toiletries, 1994, vol. 109, No. 11, pp. 55–61.

* cited by examiner

*Primary Examiner*—Shelley A. Dodson
(74) *Attorney, Agent, or Firm*—Ohlandt, Greeley, Ruggiero & Perle, LLP

(57) ABSTRACT

The present invention provides a sunless tanning composition having (a) a sunless tanning agent selected from the group consisting of: dihydroxyacetone, melanin, mahakanni, erythrulose, and any mixtures thereof, and (b) an application indicator agent selected from the group consisting of: henna, caramel, and mixtures thereof. Optionally, a color fixative may be included.

20 Claims, No Drawings

SUNLESS TANNING COMPOSITIONS

This application claims priority from Provisional application Ser. No. 60/202,403, filed May 8, 2000.

BACKGROUND OF THE INVENTION

1. Field of the Invention

The present invention relates to sunless tanning compositions. Specifically, the present invention relates to sunless tanning compositions with improved color application properties.

2. Description of the Prior Art

The sun's rays are known to produce ultraviolet radiation, such as sunburn that can have detrimental effects on the skin. Excessive exposure can lead to skin wrinkling, age spots, and even skin cancer.

As people become more aware of the harmful effects of the sun, products such as sunless tanning products are gaining popularity. These products typically employ a sunless tanning agent, such as dihydroxyacetone to impart color onto the skin that provides the impression of a tan produced by exposure to the sun.

However, these products have drawbacks that make their use inconvenient and undesirable to many consumers who use such products. One problem is the time it takes for the sunless tanning agent in the composition to develop on the skin. During this time, the composition may be transferred onto clothing or other surfaces that may come in contact with the composition. Another problem is streaking. The composition must be applied evenly to prevent streaking and to allow uniform color development.

Thus, there is a need for a product that overcomes these problems by reducing and/or preventing color streaking, which subsequently results in uniform color development.

SUMMARY OF THE INVENTION

It is an object of the present invention to provide a composition that visually aids the application and distribution of the composition over the skin.

It is another object of the present invention to provide such a composition that guards against color streaking.

It is still another object of the present invention to provide such a composition that develops color uniformly over the skin.

It is a further object of the present invention to provide such a composition that will inhibit color rub-off.

To accomplish the foregoing objects and advantages, the present invention, in brief summary, is a sunless tanning composition having (a) a sunless tanning agent selected from the group consisting of: dihydroxyacetone, melanin, mahakanni, erythrulose, and mixtures thereof, and (b) an application indicator agent selected from the group consisting of: henna, caramel, and mixtures thereof. Optionally, a color fixative may be included.

The present invention also includes a method of coloring human skin. The method comprises the steps of (a) applying to the skin, a composition comprising a sunless tanning agent selected from the group consisting of: dihydroxyacetone, melanin, mahakanni, erythrulose, and mixtures thereof; and an application indicator agent selected from the group consisting of: henna, caramel, and mixtures thereof; and (b) spreading the composition over the skin.

DETAILED DESCRIPTION OF THE INVENTION

The present invention is a sunless tanning composition that visually assists a consumer in applying the composition over the skin.

The present invention includes a sunless tanning agent as an essential component. The sunless tanning agent, also known as a self-tanning agent, imparts color to a surface, such as human skin, when applied. The sunless tanning agent may be, for example, dihydroxyacetone, melanin, mahakanni (eclipta alba), erythrulose, or any mixtures thereof. The preferred sunless tanning agent is dihydroxyacetone. Dihydroxyacetone (DHA) is an aliphatic ketone that is commonly used to color the skin. The reaction between dihydroxyacetone and the proteins in the skin leads to the appearance of tanned skin. Typically, the reaction requires at least 2 hours.

In the present invention, the total amount of sunless tanning agent in the compositions is from about 0.1 percent by weight (wt. %) to about 20 wt. %, preferably from about 0.15 wt. % to about 10 wt. %, and most preferably from about 0.25 wt. % to about 5 wt. %, of the total weight of the composition.

The present invention also includes an application indicator agent. The application indicator agent colors a surface, such as human skin, when applied. It colors the skin as the composition is applied and, thus, acts as a visual aid during application. This visual aid enables the consumer to apply the sunless tanning composition evenly and uniformly.

The total amount of application indicator agent that may be included in the compositions of the present invention is from about 0.05 wt. % to about 20 wt. %, preferably from about 0.2 wt. % to about 10 wt. %, and most preferably from about 0.25 wt. % to about 5 wt. % of the total weight of the composition.

Application indicator agents suitable for use in the present compositions include one or more hennas, caramels, malva extracts, hibiscus extracts, tyrosines, green teas, glyceraldehydes, ginsengs, erythruloses, ferric compounds, annattos, ultramarine pigments, beta-carotenes, carmins, chromium oxides, D&C water soluble dyes, bismuth compounds, FD&C water soluble dyes, copper powders, guanines, walnut extracts, iron oxides, micas, extracts which impart color, or any mixtures thereof. The preferred application indicator agents are hennas, caramels, or mixtures thereof.

While the application indicator agent is primarily used as a visual aid during application of the composition, the agent, and in particular henna, may also impart skin coloring, in addition to the skin coloring provided by the sunless tanning agent used in the compositions of the present invention.

The pH of each composition of the present invention is from about 2.5 to about 7.5. In this pH range, dihydroxyacetone is effective and exhibits good stability. Preferably, the pH is from about 3.5 to about 5.8. The pH can be adjusted within this range by the addition of a stabilizer/pH controller. The stabilizer/pH controller stabilizes the composition and controls the pH of the composition.

An optional component that may be included in the composition of the present invention is a color fixative. The color fixative may be any compound that has one or more of the following properties: facilitates or enhances color retention on a surface, inhibits rub-off, guards against color streaking, or provides uniform color development on the skin. Suitable color fixatives include, for example, binders, viscosity agents, and film formers. The more preferred color fixative is a film former.

Preferably, the film former, color fixative includes, for example, urethane polymers, derivatives of polyvinyl methylether (PVM) polymers such as polyvinyl methylether/maleic anhydride (PVM/MA) and esters thereof, polyvinylpyrrolidinone (PVP) derivatives such as polyvinylpyrrolidinone/vinyl acetate (PVP/VA), PVP, PVP/eicosene, decadiene, decene, hexadecene, styrene, propionate, polycarbamyl, maleic, vinyl acetate and methacrylates, acrylic polymers such as epoxypropyl diethyltriamine and dimethylaminohydroxypropyl copolymers, or any mixtures thereof.

The film former, color fixative may be a polyacrylates-g-polysiloxane polymer. This polymer is sold by 3M Corporation under the tradename 3M Silicone Plus SA70 Polymer 23% SA 70 in D5 Film Forming Polymer.

The urethane polymers suitable for use in the present invention include, for example, hydrophilic urethane and vinylpyrrolidone polymer or copolymer. Particularly preferred are urethane polymers sold by Hydromer, Inc. under the tradename AQUAMERE HYDROGEL. These polymers include PVP/polycarbamyl/polyglycol ester, PVP/dimethiconylacrylate/polycarbamyl/polyglycol ester, and PVP/dimethylaminoethylmethacrylate/polycarbamyl/polyglycol ester. These urethane polymers may be used by themselves or in combination with other color fixatives.

The compositions of the present invention include color fixative in an amount from about 0.1 wt. % to about 15 wt. %, preferably from about 0.25 wt. % to about 10 wt. %, and most preferably from about 0.5 wt. % to about 5 wt. %, of the total weight of the composition.

A preferred composition of the present invention will contain from about 0.1 wt. % to about 20 wt. % of a sunless tanning agent and about 0.05 wt. % to about 20 wt. % of an application indicator agent. A more preferred composition of the present invention will contain from about 0.15 wt. % to about 10 wt. % of a sunless tanning agent and about 0.2 wt. % to about 10 wt. % of an application indicator agent.

The most preferred embodiment of the present invention is a sunless tanning composition that includes from about 0.25 wt. % to about 8 wt. % of dihydroxyacetone, about 0.05 wt. % to about 10 wt. % of henna, about 0.15 wt. % to about 10 wt. % of caramel, and about 0.5 wt. % to about 5 wt. % of a color fixative.

In addition, the composition of the present invention may also include one or more skin conditioning agents. Preferably, the skin conditioning agents include, for example, phenyl trimethicone, aloe vera gel, dimethicone, petrolatum, cocoa butter, glycerin, allantoin, sodium PCA, or any mixtures thereof. The skin conditioning agent is preferably about 0.1 wt. % to about 10 wt. % of the total weight of the composition.

The compositions of the present invention may also contain one or more humectants, such as, butylene glycol, propylene glycol, and caprylic/capric triglyceride; emollients, such as, glycereth-7 benzoate, myreth-3 octanoate, and C12–C15 alkyl benzoate; emulsifiers, such as, poloxamer 182, PEG-40 castor oil, glyceryl stearate, PEG-100 stearate, stearic acid, PEG-7 glyceryl cocoate, steareth-20, steareth-2, cetyl alcohol, and stearyl alcohol; surfactants, such as, PEG-8 laurate and cocamidopropyl betaine; preservatives, such as, phenoxyethanol and hydroxybenzoate esters; antioxidants, such as, tocopherol; and/or chelating agents, such as, disodium EDTA. The humectants, emollients, surfactants, preservatives, antioxidants, or chelating agents, are each about 0.1 wt. % to about 15 wt. % of the total weight of the composition.

One or more solvents may also be included in the present composition. Suitable solvents include, for example, water, ethoxydiglycol, dimethyl isosorbide, or mixtures thereof. The solvents are present in an amount about 50 wt. % to about 90 wt. %.

The compositions of the present invention can also contain one or more additional components commonly used in skin compositions. Such additional components include, but are not limited to, fragrances, citric acid, ascorbic acid, xanthan gum, or combinations thereof. These additional components are present in an amount about 0.01 wt. % to about 5 wt. % of the total weight of the composition.

The present invention also includes a method for coloring human skin. The method comprises the steps of (a) applying to the skin, a composition comprising a sunless tanning agent selected from the group consisting of: dihydroxyacetone, melanin, mahakanni, erythrulose, and any mixtures thereof; and an application indicator agent selected from the group consisting of: henna, caramel, and mixtures thereof; and (b) spreading the composition over the skin.

Having thus described the present invention with particular reference to preferred embodiments thereof it will be apparent that various changes and modifications may be made therein without departing from the spirit and scope of the present invention as defined in the appended claims.

What is claimed is:

1. A sunless tanning composition comprising:
   a sunless tanning agent selected from the group consisting of: dihydroxyacetone, melanin, mahakanni, erythrulose, and any mixtures thereof; and
   an application indicator agent comprising henna.

2. The composition of claim 1, wherein said sunless tanning agent is dihydroxyacetone.

3. The composition of claim 1, wherein said sunless tanning agent is about 0.1 wt. % to about 20 wt. % of the total weight of the composition.

4. The composition of claim 1, wherein said application indicator agent further comprises caramel.

5. The composition of claim 1, wherein said application indicator agent is about 0.05 wt. % to about 20 wt. % of the total weight of the composition.

6. The composition of claim 5, wherein said application indicator agent is about 0.2 wt. % to about 10 wt. % of the total weight of the composition.

7. The composition of claim 1, wherein said composition has a pH of about 2.5 to about 7.5.

8. The composition of claim 1, further comprising a color fixative.

9. The composition of claim 8, wherein said color fixative is a urethane polymer.

10. The composition of claim 9, wherein said urethane polymer is a hydrophilic urethane and vinylpyrrolidone polymer or copolymer.

11. The composition of claim 9, wherein said urethane polymer is selected from the group consisting of: PVP/polycarbamyl/polyglycol ester, PVP/dimethiconylacrylate/polycarbamyl/polyglycol ester, PVP/dimethylaminoethylmethacrylate/polycarbamyl/polyglycol ester, and mixtures thereof.

12. The composition of claim 8, wherein said color fixative is a polyacrylates-g-polysiloxane polymer.

13. The composition of claim 8, wherein said color fixative is about 0.1 wt. % to about 15 wt. % of the total weight of the composition.

14. The composition of claim 1, further comprising an ingredient selected from the group consisting of: skin conditioning agents, humectants, emollients, emulsifiers, surfactants, antioxidants, chelating agents, solvents, and any combinations thereof.

15. The composition of claim 1, further comprising an ingredient selected from the group consisting of: fragrances, citric acid, ascorbic acid, xanthum gum, and any combinations thereof.

16. A sunless tanning composition comprising:
   from about 0.1 to about 20 wt. % of a sunless tanning agent selected from the group consisting of: dihydroxyacetone, melanin, mahakanni, erythrulose, and any mixtures thereof; and
   from about 0.05 to about 20 wt. % of an application indicator agent comprising henna.

17. A method of coloring human skin, comprising the steps of:
   a) applying to the skin a composition comprising a sunless tanning agent selected from the group consisting of: dihydroxyacetone, melanin, mahakanni, erythrulose, and any mixtures thereof; and an application indicator agent comprising henna; and
   b) spreading said composition over the skin.

18. The composition of claim 17, further comprising a color fixative.

19. The composition of claim 16, wherein said application indicator agent further comprises caramel.

20. The composition of claim 17, wherein said application indicator agent further comprises caramel.

* * * * *